United States Patent [19]

Roobeek et al.

[11] 4,166,076

[45] Aug. 28, 1979

[54] CYCLODIMERIZATION OF ISOPRENE

[75] Inventors: Cornelis F. Roobeek; Petrus W. N. M. van Leeuwen, both of Amsterdam, Netherlands

[73] Assignee: Shell Oil Company, Houston, Tex.

[21] Appl. No.: 869,563

[22] Filed: Jan. 16, 1978

[30] Foreign Application Priority Data

Jan. 19, 1977 [GB] United Kingdom ................ 2100/77

[51] Int. Cl.$^2$ .......................... C07C 3/21; C07C 3/035
[52] U.S. Cl. .................................... 585/369; 585/366; 585/370
[58] Field of Search .................... 260/666 A, 666 B

[56] References Cited

U.S. PATENT DOCUMENTS 3,187,062  6/1965  Shechter .......................... 260/666 B
3,792,101  2/1974  Hattori et al. .................... 260/666 B

OTHER PUBLICATIONS

Chem. Ab. 80: 120396g, 1974.

Primary Examiner—Veronica O'Keefe
Attorney, Agent, or Firm—Howard W. Haworth; Ronald L. Clendenen

[57] ABSTRACT 1,5-Dimethyl-1,5-cyclooctadiene and 1,4-dimethyl-4-vinyl-1-cyclohexene are prepared by contacting isoprene with a catalyst obtained by mixing a nickel compound, a reducing agent capable of reducing the nickel to zerovalent nickel, and a trihydrocarbyl phosphite, arsenite or antimonite wherein at least one of the three hydrocarbyl groups is a substituted hydrocarbyl group $CF_3—(CF_2)_nC(H)(R)—$, in which $n \geq 0$ and R is an optionally substituted hydrocarbyl group. Only very small amounts of the undesired 1,6-dimethyl-1,5-cyclooctadiene are formed.

16 Claims, No Drawings

CYCLODIMERIZATION OF ISOPRENE

BACKGROUND OF THE INVENTION

1. Field of the Invention

This invention relates to a process for the preparation of 1,5-dimethyl-1,5-cyclooctadiene and 1,4-dimethyl-4-vinyl-1-cyclohexene from isoprene.

2. Description of the Prior Art 1,5-Dimethyl-1,5-cyclooctadiene is an intermediate in the synthesis of Vitamin E, see British patent applications Nos. 49796/74 and 5091/75, the aroma chemicals 7-hydroxy-3,7-dimethyl-1-o-octene (dihydromyrcenol), see British patent application No. 4371/76, and alphalinalool and linalool, see British patent application No. 45309/76.

1,4-Dimethyl-4-vinyl-1-cyclohexene is an intermediate in the synthesis of aroma chemicals having characteristic floral odors, see British patent application No. 33050/76, and woody odors, see British patent application No. 7818/76.

1,5-Dimethyl-1,5-cyclooctadiene was formed by contacting isoprene with a mixture obtained by combining a solution of nickel acetylacetonate and triphenyl phosphine in benzene with a solution of ethoxydiethylaluminum in benzene, see Example 61 of French patent specification No. 1,283,217. A disadvantage of this known process is that a mixture of 70% 1,5-dimethyl-1,5-cyclooctadiene and 30% 1,6-dimethyl-1,5-cyclooctadiene was formed. As 1,6-dimethyl-1,5-cyclooctadiene is not an intermediate in the synthesis mentioned hereinbefore it should be separated from the 1,5-dimethyl-1,5-cyclooctadiene. However, such a separation of these materials is very difficult, their boiling points being close to each other. Therefore, a process in which hardly any 1,6-dimethyl-1,5-cyclooctadiene is formed, if at all, would be very attractive.

U.S. Pat. No. 3,436,431 issued Apr. 1, 1969, to Candlin et al, U.S. Pat. No. 3,522,321 issued July 28, 1970, to DeYoung, Chem. Abstracts 60 (1964) 11883e, Chem. Abstracts 66 (1967) 28422a and Chem. Abstracts 80 (1974) 120396g are references which disclose the dimerization of isoprene in the presence of a complexed group VIII metal. These references do not however use the particular complexing agent of this invention, nor is the content of 1,6-dimethyl-1,5-cyclooctadiene maintained at as low levels as in the instant process.

SUMMARY OF THE INVENTION

It has been found that the use as a catalyst for dimerizing isoprene of a certain group of substituted trihydrocarbyl phosphites, substituted trihydrocarbyl arsenites or substituted trihydrocarbyl antimonites instead of triphenylphosphine complexed with a Group VIII metal results in a very low selectivity to the undesired 1,6-dimethyl-1,5-cyclooctadiene and a very high overall selectivity to 1,5-dimethyl-1,5-cyclooctadiene and 1,4-dimethyl-4-vinyl-1-cyclohexene. The latter two compounds can easily be separated from each other by means of distillation.

DESCRIPTION OF THE PREFERRED EMBODIMENTS

Accordingly, the invention relates to a process for the preparation of 1,5-dimethyl-1,5-cyclooctadiene and 1,4-dimethyl-4-vinyl-1-cyclohexene, which comprises contacting isoprene with a catalyst obtained by mixing (a) a substituted trihydrocarbyl phosphite, substituted trihydrocarbyl arsenite or substituted trihydrocarbyl antimonite, wherein at least one of the three hydrocarbyl groups is a substituted hydrocarbyl group of the general formula $$CF_3-(CF_2)_n-C(H)(R)-, \quad (I)$$

wherein n is equal to zero or an integer of at least one and R represents a substituted or unsubstituted hydrocarbyl group, and (b) a compound of a metal of Group VIII of the Periodic Table of the Elements in which the metal has an oxidation number of zero.

The 1,5-dimethyl-1,5-cyclooctadiene and 1,4-dimethyl-4-vinyl-1-cyclohexene formed according to the present invention may be isolated from the reaction mixture in any desired manner, for example, by washing with dilute aqueous hydrochloric acid to remove inorganic material, separation of the organic phase from the acidic aqueous phase and distillation of the separated organic phase to yield a distillate of 1,5-dimethyl-1,5-cyclooctadiene and a distillate of 1,4-dimethyl-4-vinyl-1-cyclohexene. Surprisingly, the isolated 1,5-dimethyl-1,5-cyclooctadiene has such a high purity that it can be used without purification in the synthesis mentioned hereinbefore. The valuable 1,4-dimethyl-4-vinyl-1-cyclohexene is co-produced with an attractive selectivity. The expression "purity of 1,5-dimethyl-1,5-cyclooctadiene", given in a percentage, is defined as $$c/c+d\times 100,$$

wherein c is the selectivity to 1,5-dimethyl-1,5-cyclooctadiene and d is the selectivity to 1,6-dimethyl-1,5-cyclooctadiene.

The expression "selectivity to compound X", given in a percentage, is defined as $$a/b\times 100,$$

wherein a is the amount of isoprene converted into compound X, and b is the amount of the converted isoprene.

The figure n in formula I may be equal to, for example, 0, 1, 2, 3, 4, or 5. Very good results have been obtained in cases where n is equal to zero.

The hydrocarbyl group represented by R in formula I may be, for example, an alkyl, a cycloalkyl or an aryl group. Examples of these hydrocarbyl groups are methyl, ethyl, propyl, isopropyl, cyclohexyl and phenyl groups. Each of these hydrocarbyl groups may be substituted. Examples of substituents are fluorine, chlorine and bromine atoms and alkoxy and phenoxy groups.

It has been found that an increasing number of trifluoromethyl groups in the group of formula I decreases the selectivity to the undesired 1,6-dimethyl-1,5-cyclooctadiene and increases the selectivity to the desired 1,4-dimethyl-4-vinyl-1-cyclohexene, with retention of the good selectivity to the other desired compound 1,5-dimethyl-1,5-cyclooctadiene. Thus, good results are obtained when at least two trifluoromethyl groups in the substituted trihydrocarbyl phosphite, substituted trihydrocarbyl arsenite or substituted trihydrocarbyl antimonite are bound to one or two

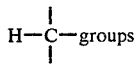

one of which is shown in formula I. The latter group is, of course, also bound to an oxygen atom of the phosphite, arsenite or antimonite. Examples of such substituted trihydrocarbyl phosphites are
di(2,2,2-trifluoro-1-phenylethyl) phenyl phosphite,
di(2,2,2-trifluoro-1-phenylethyl) methyl phosphite and
di(2,2,2-trifluoro-1-phenylethyl) isopropyl phosphite.

Good results have been obtained with diphenyl 2,2,2-tri-fluoro-1-(trifluoromethyl)ethyl phosphite.

Better results are obtained when at least three trifluoromethyl groups in the substituted trihydrocarbyl phosphite, substituted trihydrocarbyl arsenite or substituted trihydrocarbyl antimonite are bound to

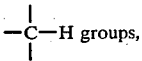

one of which is shown in formula I. Examples of such substituted trihydrocarbyl phosphites are
phenyl 2,2,2-trifluoro-1-phenylethyl 2,2,2-trifluoro-1-(trifluoromethyl)ethyl phosphite,
isopropyl 2,2,2-trifluoro-1-phenylethyl-2,2,2-trifluoro-1-(trifluoromethyl)ethyl phosphite and
2,2,2-trifluoro-1-methylethyl di(2,2,2-trifluoro-1-phenylethyl) phosphite.

Very good results have been obtained with tri(2,2,2-trifluoro-1-phenylethyl) phosphite.

Even better results are obtained when at least four trifluoromethyl groups in the substituted trihydrocarbyl phosphite, substituted trihydrocarbyl arsenite or substituted trihydrocarbyl antimonite are bound to

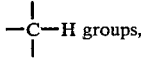

one of which is shown in formula I. Examples of such substituted trihydrocarbyl phosphites are
di(2,2,2-trifluoro-1-phenylethyl) 2,2,2-trifluoro-1-(trifluoromethyl)ethyl phosphite,
2,2,2-trifluoro-1-methylethyl 2,2,2-trifluoro-1-phenylethyl 2,2,2-trifluoro-1-(trifluoromethyl)ethyl phosphite and
methyl di [2,2,2-trifluoro-1-(trifluoromethyl)ethyl]phosphite.

Very good results have been obtained with phenyl di[2,2,2-trifluoro-1-(trifluoromethyl)ethyl]phosphite.

The best results are obtained when at least five trifluoromethyl groups in the substituted trihydrocarbyl phosphite, substituted trihydrocarbyl arsenite or substituted trihydrocarbyl antimonite are bound to

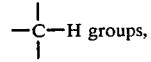

one of which is shown in formula I. Examples of such substituted trihydrocarbyl phosphites are
2,2,2-trifluoro-1-phenylethyl di[2,2,2-trifluoro-1-(trifluoromethyl)ethyl]phosphite and
2,2,2-trifluoro-1-methylethyl di[2,2,2-trifluoro-1-(trifluoromethyl)ethyl]phosphite.

Excellent results have been obtained with tri[2,2,2-trifluoro-1-(trifluoromethyl)ethyl]phosphite.

The temperature at which the process is carried out is not critical and may vary within wide limits. The process is preferably carried out at a temperature in the range of from about 0° C. to about 200° C. With tri[2,2,2-trifluoro-1-(trifluoromethyl)ethyl] phosphite the reaction can be carried out at relatively low temperatures, preferably in the range of from about 15° C. to about 40° C., giving particularly low selectivities to 1,6-dimethyl-1,5-cyclooctadiene and particularly high selectivities to 1,5-dimethyl-1,5-cyclooctadiene and 1,4-dimethyl-4-vinyl-1-cyclohexene. With this substituted trihydrocarbyl phosphite, the reaction is suitably carried out at ambient temperature.

The molar ratio of isoprene to the metal of Group VIII is not critical and may vary within wide limits. This molar ratio may be between, for example, about 10,000 and about 10.

When part of catalyst component (a) is replaced by a triaryl phosphite, triaryl arsenite or triaryl antimonite, the total amount of phosphorus, arsenic or antimony being kept constant, the selectivity to 1,5-dimethyl-1,5-cyclooctadiene can be considerably increased (at the expense of the selectivity to 1,4-dimethyl-4-vinyl-1-cyclooctene) and 1,5-dimethyl-1,5-cyclooctadiene can be isolated in a slightly purer state. Examples of aryl groups are phenyl, p-tolyl, 2,3-xylyl and 1-naphthyl groups. Very good results have been obtained with phenyl groups.

Although the Applicants do not wish to bind themselves to an explanation of the present process, they believe that the product obtained by mixing (a) and (b) is a complex chemical compound, which is the catalyst. Although this complex chemical compound may be isolated and then contacted with isoprene, this is not necessary; without isolation the process proceeds smoothly and efficiently.

The compound of a metal of Group VIII of the Periodic Table of the Elements in which the metal has an oxidation number of zero is preferably made in situ by mixing (c) a compound of a metal of Group VIII of the Periodic Table of the Elements in which the metal has an oxidation number higher than zero, and (d) a reducing agent decreasing the oxidation number of the metal in the compound sub (c) to zero.

Among the Group VIII metals used as a starting material—i.e. nickel, cobalt, iron, ruthenium, rhodium, palladium, osmium, iridium and platinum—nickel has given very good results. The starting nickel compound may have an oxidation number of 0, 1, 2, 3 or 4. For the concept of "oxidation number" reference is made to "Inorganic Chemistry, A Concise Text" (1965), by J. Bassett, pp. 106–109. A reducing agent need not be used when the starting nickel compound has an oxidation number of zero, as is the case in, for example, $Ni(CO)_4$, $Ni(PF_3)_4$, $Ni(PCl_3)_4$ or $Ni[P(OC_6H_5)_3]_4$. Examples of nickel compounds in which the nickel has an oxidation number higher than zero are nickel acetylacetonate, $Ni[P(C_6H_5)_3]Br$, $NiBr_2[P(C_6H_5)_3]_2$, $NiCl_2[P(C_6H_5)_3]_2$, $KNiF_3$, $NiBr_3[P(C_6H_5)_3]_2$ and $K_2NiF_6$. Further examples of such nickel compounds can be found in British patent specification No. 1,000,477, which also describes a large number of reducing agents.

The process may be conducted in the presence of a solvent. This solvent must be inert with regard to the compounds involved in the process. Examples of such solvents are aromatic, cycloaliphatic and aliphatic hydrocarbons and tetrahydrofura, N-methylpyrrolidone and diethyl ether. Mixtures of these solvents may be used, for example, mixtures of tetrahydrofuran and aliphatic hydrocarbons or of tetrahydrofuran and N-methylpyrrolidone. Isoprene itself may also be used as a solvent.

The process may be carried out by adding a solution of a reducing agent sub (d) with stirring to a mixture of a compound sub (c), a compound sub (a), isoprene and a solvent, followed by heating, if necessary.

The preparation of 1,5-dimethyl-1,5-cyclooctadiene proceeds via 1-methyl-4-isopropenyl-1-vinylcyclobutane, which, above room temperature, rearranges to 1,5-dimethyl-1,5-cyclooctadiene. 1-Methyl-4-isopropenyl-1-vinylcyclobutane may be isolated from the reaction mixture as described in Journal of the American Chemical Society 95 (1973)3438–3439.

The above-mentioned process for the preparation of novel catalysts comprises mixing (a) a substituted trihydrocarbyl phosphite, substituted trihydrocarbyl arsenite or substituted trihydrocarbyl antimonite, wherein at least one of the three hydrocarbyl groups is a substituted hydrocarbyl group of the general formula

$$CF_3-(CF_2)_n-C(H)(R)-, \qquad (I)$$

wherein n is equal to zero or an integer of at least one and R represents a substituted or unsubstituted hydrocarbyl group, and (b) a nickel compound in which the nickel has an oxidation number of zero.

Substituted trihydrocarbyl phosphites, substituted trihydrocarbyl arsenites or substituted trihydrocarbyl antimonites, wherein at least one of the three hydrocarbyl groups is a substituted hydrocarbyl group of the general formula

$$CF_3-(CF_2)_n-C(H)(R)-, \qquad (I)$$

wherein n is equal to zero or an integer of at least one and R represents a substituted or unsubstituted hydrocarbyl group, with the proviso that not all three hydrocarbyl groups in the substituted trihydrocarbyl phosphites are equal substituted hydrocarbyl groups of formula I, are the novel esters referred to hereinbefore.

The said novel substituted trihydrocarbyl phosphites, substituted trihydrocarbyl arsenites and substituted trihydrocarbyl antimonites may be prepared by reacting an alcohol of the general formula

$$CF_3-(CF_2)_n-C(H)(R)OH, \qquad (II)$$

wherein n and R have the same meaning as in formula I, with a compound of the general formula

$$Z(R^1)(R^2)(R^3), \qquad (III)$$

wherein each of the symbols $R^1$, $R^2$ and $R^3$ represents a halogen atom or a substituted or unsubstituted hydrocarbyloxy group and Z a phosphorus, arsenic or antimony atom, in the presence of an acid acceptor.

The invention will be further described by the following illustrative embodiments which are provided for illustration and are not to be construed as limiting the invention.

ILLUSTRATIVE EMBODIMENTS

Examples I–V

A 100-ml A.I.S.I. 316 stainless steel autoclave, kept at a temperature of 0° C., was flushed with nitrogen and then charged with, consecutively, 0.5 mmol of nickel acetylacetonate dissolved in 4 ml of tetrahydrofuran, an amount of a triorgano phosphite—see column 2 of the Table—corresponding to the molar ratio stated in column 3 of the Table, 2.0 mmol of N-methylpyrrolidone, 500 mmol of isoprene and a solution of 3 mmol of triethylaluminium in 10 ml of 2,2,4-trimethylpentane. Then the autoclave was closed and heated to the temperature stated in column 4 and kept at this temperature for the time stated in column 5 of the Table. Subsequently, the conversion of isoprene and the selectivities to compounds A, B and C were determined by means of gas-liquid chromatography, see column 6–9 in the Table. Column 10 presents the purity of A; (the purity of A is defined hereinbefore).

Compounds A, B and C are:
A = 1,5-dimethyl-1,5-cyclooctadiene,
B = 1,6-dimethyl-1,5-cyclooctadiene and
C = 1,4-dimethyl-4-vinyl-1-cyclohexene.

Nine experiments were carried out in the manner described above: the experiments of Examples I–V and the Comparative Experiments A–D, see Table. An "x" indicates that the determination has not been carried out.

Table

| 1 | 2 | 3 | 4 | 5 | 6 | 7 | 8 | 9 | 10 |
|---|---|---|---|---|---|---|---|---|---|
| | | Molar ratio P/Ni | Temperature °C. | Time, h | Conversion of isoprene, g | Selectivity, %, to | | | Purity of A, % |
| | Triorgano phosphite | | | | | A | B | C | |
| Example I | tri[2,2,2-trifluoro-1-(trifluoromethyl)ethyl] | 1 | 22 | 120 | >95 | 29.1 | 0.9 | 60 | 97.0 |
| Example II | " | 3 | 105 | 0.3 | >97 | 16.3 | 1.4 | 59 | 92.1 |
| Example III | phenyl di[2,2,2-trifluoro-1-(trifluoromethyl)ethyl] | 3 | 105 | 2 | >99 | 43.7 | 3.3 | 39 | 93.0 |
| Example IV | tri(2,2,2-trifluoro 1-phenylethyl) | 3 | 105 | 5.5 | 55 | 45.9 | 5.1 | 23 | 90.0 |
| Example V | diphenyl 2,2,2-trifluoro-1-(trifluoromethyl)ethyl | 3 | 105 | 2 | >99 | 56.3 | 7.2 | 19 | 88.7 |

Table-continued

| 1 | 2 | 3 | 4 | 5 | 6 | 7 | 8 | 9 | 10 |
|---|---|---|---|---|---|---|---|---|---|
|   |   |   |   |   | Conversion of i- | Selectivity, %, to | | | |
|   | Triorgano phosphite | Molar ratio P/Ni | Temperature °C. | Time, h | soprene, g | A | B | C | Purity of A, % |
| Comparative experiment A | triphenyl | 3 | 105 | 5 | 74 | 46.2 | 13.0 | 7.2 | 78.0 |
| Comparative experiment B | tri(2,2,2-trifluoroethyl) | 3 | 105 | 5 | <5 | x | x | x | x |
| Comparative experiment C | tri[2-Caloro-1-(Chloromethyl)ethyl] | 3 | 105 | 4.5 | 10 | x | x | x | x |
| Comparative experiment D | triisopropyl | 3 | 105 | 21 | 99 | 26.2 | 21.4 | 13 | 55.0 |

EXAMPLE VI

The experiment of Example II was repeated, with the exception that instead of 1.5 mmol of tri[2,2,2-trifluoro-1-(trifluoromethyl)ethyl]phosphite, a mixture of 0.5 mmol of this compound and 1.0 mmol of triphenyl phosphite was used. After a reaction time of 1.5 hours the conversion of isoprene was more than 99% with selectivities to compounds A, B and C of 47.2%, 3.5% and 31%, respectively, giving a purity of compound A of 93.1%. Comparison of these results with those of Example II shows that the use of triphenyl phosphite has considerably increased the selectivity to A and has slightly increased the purity of A. Comparison of the results of Example VI with those of the Comparative Experiment A shows that the use of tri[2,2,2-trifluoro-1-(trifluoromethyl)ethyl]phosphite has considerably increased the purity of A and the selectivity to C.

EXAMPLE VII

Preparation of phenyl di[2,2,2-trifluoro-1-(trifluoromethyl)ethyl]phosphite

A mixture of 6 mol of phosphorus trichloride and 1 mol of phenol was heated under reflux for four hours. The reaction mixture thus formed was distilled to isolate the phenyl dichlorophosphite —PCl$_2$(OC$_6$H$_5$)— formed. A freshly distilled amount of 59 mmol of phenyl dichlorophosphite was stirred into 50 ml of diethyl ether and after the temperature had been lowered to −20° C., a solution of 12.2 ml of 1,1,1,3,3,3-hexafluoro-2-propanol and 9.5 ml of pyridine in 150 ml of diethyl ether was added. The mixture thus formed was allowed to adopt a temperature of 22° C. while being stirred and kept overnight at this temperature. The precipitate formed was filtered off, the solvent was evaporated from the filtrate giving a residue which was distilled at sub-atmospheric pressure to isolate the title compound in a yield of 20%, calculated on starting phenyl dichlorophosphite. The title compound had a boiling point of 110° C. at 20 mmHg.

EXAMPLE VIII

Preparation of tri(2,2,2-trifluoro-1-phenylethyl) phosphite

A solution of 57 mmol of phosphorus trichloride in 25 ml of diethyl ether was added dropwise at a temperature of −10° C. to a solution of 170 mmol of 2,2,2-trifluoro-1-phenylethanol and 170 mmol of pyridine in 100 ml of diethyl ether. The mixture thus formed was allowed to adopt a temperature of 22° C. while being stirred and kept overnight at this temperature. The precipitate formed in the mixture was filtered off, the solvent was evaporated from the filtrate giving a residue which was distilled at sub-atmospheric pressure to isolate the title compound in a yield of 95%, calculated on starting phosphorus trichloride. The title compound boiled between 150° and 154° C. at 0.1 mmHg.

EXAMPLE IX

Preparation of diphenyl 2,2,2-trifluoro-1-(trifluoromethyl)ethyl phosphite

An amount of 28.2 mmol of 1,1,1,3,3,3-hexafluoro-2-propanol together with 0.1 mmol of solid sodium hydroxide was added to 84.6 mmol of triphenyl phosphite at a temperature of 22° C. The mixture thus formed was stirred for one hour and then heated under reflux for another hour. Then the solvent was evaporated from the mixture, giving a residue which was distilled at sub-atmospheric pressure to isolate the title compound in a yield of 18.5%, calculated on starting 1,1,1,3,3,3-hexafluoro-2-propanol.

EXAMPLE X

Tri[2,2,2-trifluoro-1-(trifluoromethyl)ethyl]phosphite (8.0 mmol) was added dropwise, with stirring, at a temperature of 0° C. to a mixture of bis(1,5-cyclooctadienyl)nickel (2.0 mmol), 2,2,4-trimethylpentane (10 ml) and 1,3-butadiene (18.6 mmol). This caused the formation of a precipitate. The temperature of the mixture was increased to 50° C. and stirring was continued during 30 min. The clear solution thus obtained was cooled to 20° C., which caused the precipitation of orange-yellow crystals. After separation by filtration and washing with 2,2,4-trimethylpentane (10 ml) the crystals had a weight of 1.3 g.

EXAMPLE XI

Example I was repeated with 0.4 g of the crystals obtained in Example X instead of the combination of 0.5 mmol of nickel acetylacetonate, the 1.5 mmol of the triorgano phosphite and the 3 mmol of triethylaluminium. The conversion of isoprene was higher than 95% and the selectivities to the compounds A, B and C were 29%, 0.9% and 60%, respectively, giving a purity of compound A of 97.0%.

What is claimed is:

1. A process for the preparation of 1,5-dimethyl-1,5-cyclooctadiene and 1,4-dimethyl-4-vinyl-1-cyclohexene, which comprises contacting isoprene with a catalyst consisting essentially of the reaction product of (a) a member of the group consisting of a substituted trihydrocarbyl phosphite, substituted trihydrocarbyl arsenite or substituted trihydrocarbyl antimonite, wherein at least one of the three hydrocarbyl groups is a substituted hydrocarbyl group of the general formula $$CF_3-(CF_2)_n-C(H)(R)-, \quad (I)$$

wherein n is equal to zero or an integer of at least one and R represents a substituted or unsubstituted hydrocarbyl group, and (b) a compound of a metal of Group VIII of the Periodic Table of the Elements in which the metal has an oxidation number of zero.

2. The process as claimed in claim 1, in which n in formula I is equal to zero.

3. The process as claimed in claim 2, in which at least two trifluoromethyl groups in the substituted trihydrocarbyl phosphite, substituted trihydrocarbyl arsenite or substituted trihydrocarbyl antimonite are bound to one or two

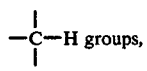

one of which is shown in formula I.

4. The process as claimed in claim 3, in which the substituted trihydrocarbyl phosphite is diphenyl 2,2,2-trifluoro-1-(trifluoromethyl)ethyl phosphite.

5. The process as claimed in claim 3, in which at least three trifluoromethyl groups in the substituted trihydrocarbyl phosphite, substituted trihydrocarbyl arsenite or substituted trihydrocarbyl antimonite are bound to

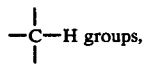

one of which is shown in formula I.

6. The process as claimed in claim 5, in which the substituted trihydrocarbyl phosphite is tri(2,2,2-trifluoro-1-phenylethyl) phosphite.

7. The process as claimed in claim 5, in which at least four trifluoromethyl groups in the substituted trihydrocarbyl phosphite, substituted trihydrocarbyl arsenite or substituted trihydrocarbyl antimonite are bound to

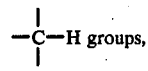

one of which is shown in formula I.

8. The process as claimed in claim 7, in which the substituted trihydrocarbyl phosphite is phenyl di[2,2,2-trifluoro-1-(trifluoromethyl)ethyl]phosphite.

9. The process as claimed in claim 7, in which at least five trifluoromethyl groups in the substituted trihydrocarbyl phosphite, substituted trihydrocarbyl arsenite or substituted trihydrocarbyl antimonite are bound to

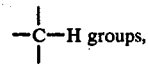

one of which is shown in formula I.

10. The process as claimed in claim 9, in which the substituted trihydrocarbyl phosphite is tri[2,2,2-trifluoro-1-(trifluoromethyl)ethyl]phosphite.

11. The process as claimed in claim 1 which is carried out at a temperature in the range of from about 0° C. to about 100° C.

12. The process as claimed in claim 10, which is carried out at a temperature in the range of from about 15° C. to about 40° C.

13. The process as claimed in claim 1, in which the catalyst has been obtained in the presence of a triaryl phosphite, triaryl arsenite or triaryl antimonite.

14. The process as claimed in claim 13, in which the catalyst has been obtained in the presence of triphenyl phosphite.

15. The process as claimed in claim 1, in which the compound of a metal of Group VIII of the Periodic Table of the Elements in which the metal has an oxidation number of zero is made in situ by mixing (c) a compound of a metal of Group VIII in which the metal has an oxidation number higher than zero, and (d) a reducing agent decreasing the oxidation number of the metal in the compound sub (c) to zero.

16. The process as claimed in claim 1, in which nickel is used as the metal of Group VIII.

* * * * *